United States Patent [19]

Johnson

[11] Patent Number: 4,682,593

[45] Date of Patent: Jul. 28, 1987

[54] ADJUSTABLE BREAST BRIDGE FOR USE IN MULTIPLE-PLANE INTERSTITIAL BREAST IMPLANTS

[76] Inventor: Douglas W. Johnson, 8265 Riding Club Rd., Jacksonville, Fla. 33216

[21] Appl. No.: 435,514

[22] Filed: Oct. 20, 1982

[51] Int. Cl.⁴ ............................................. A61B 17/00
[52] U.S. Cl. ................................................. 128/303 R
[58] Field of Search ............... 128/316, 319 R, 303 R; 33/21 R, 21 B, 21 D, 42, 9 R

[56] References Cited

U.S. PATENT DOCUMENTS

| 899,202 | 9/1908 | Byrd et al. | 33/9 R |
| 905,723 | 12/1908 | Longnecker | 33/9 R |
| 1,254,986 | 1/1918 | Conlon et al. | 33/42 |

Primary Examiner—Edward M. Coven
Attorney, Agent, or Firm—John R. Flanagan; Donald J. Singer

[57] ABSTRACT

An adjustable breast bridge includes a pair of upright members, a rectangular span member, adjustable fasteners connecting the support members and span member together in an inverted U-shaped configuration in which the bridge is adapted to straddle a breast of any size. Each support member has a vertically adjustable slot which can be raised or lowered as desired to any desired distance above the base of the bridge, as indicated by millimeter calibrations on the outer sides of the support members. The marking tool can be inserted through the support member slots and used to draw a line on the breast surface a precise distance above and parallel to the base of the bridge.

9 Claims, 10 Drawing Figures

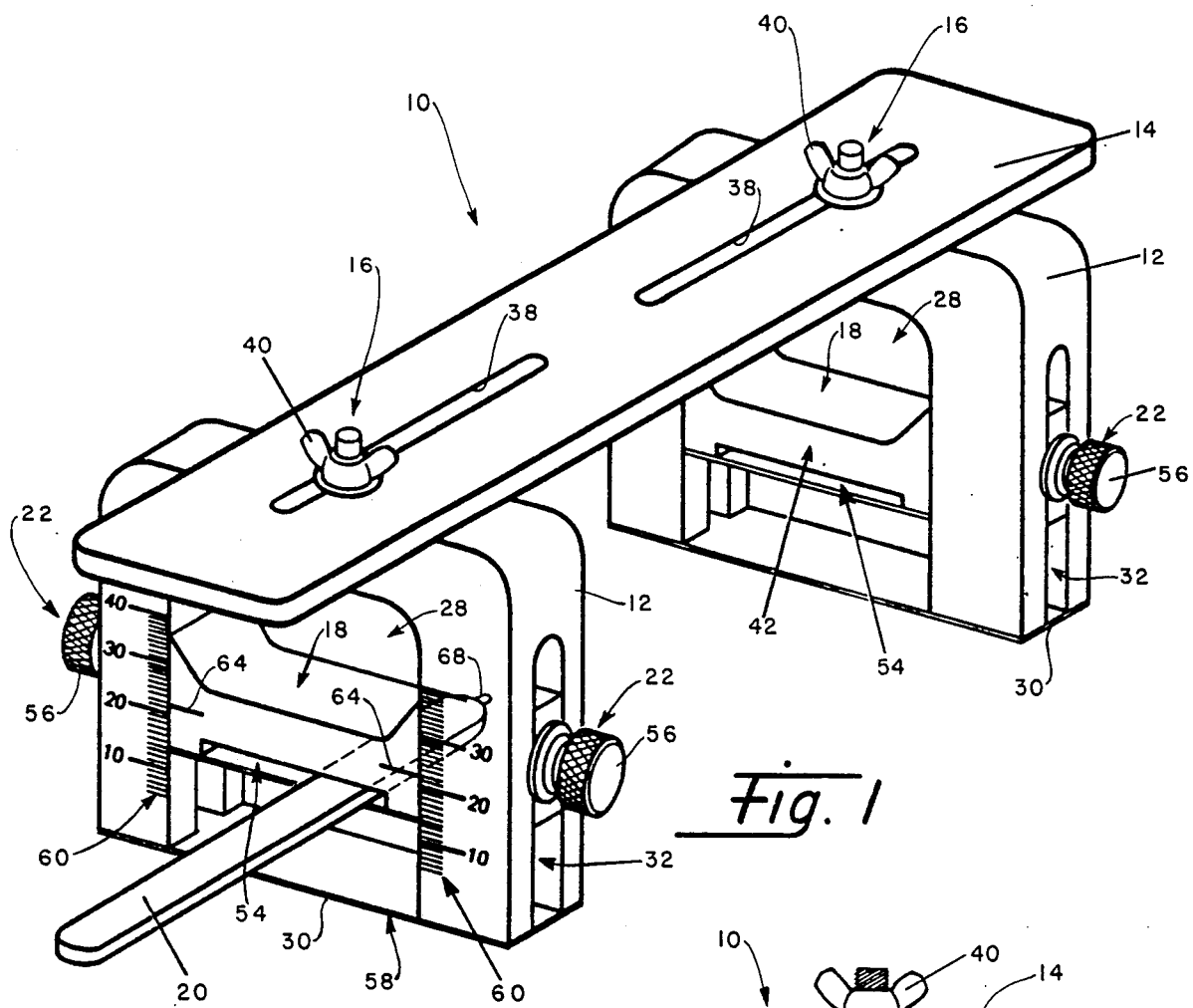
Fig. 1
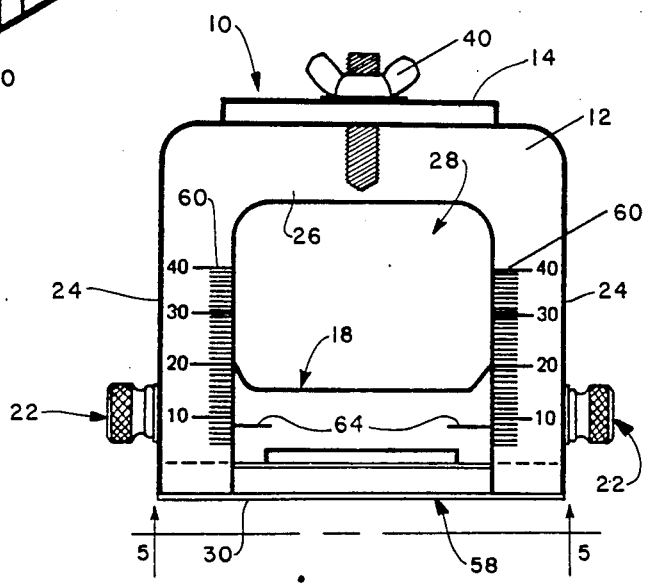
Fig. 4
Fig. 5

ADJUSTABLE BREAST BRIDGE FOR USE IN MULTIPLE-PLANE INTERSTITIAL BREAST IMPLANTS

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention broadly relates to breast cancer treatment and, more particularly, is concerned with an adjustable breast bridge used for patients requiring multiple-plane interstitial radioisotope breast implants.

2. Description of the Prior Art

Breast cancer afflicts thousands of women each year in the United States. Complete removal of the breast, or radical mastectomy, has heretofore been the traditional treatment modality for breast cancer in many patients.

However, a newer treatment which entails surgical removal of the malignant tumor mass followed by radiation therapy to the remaining breast tissue has more recently been accepted as an alternative to mastectomy for selected patients. This radiation is usually delivered by combining external beam therapy with interstitial radioisotope implants.

Radioisotope implants are performed by placing a series of hollow nylon tubes through the breast tissue to form an interstitial plane. These tubes are afterloaded with radioisotopes of varying strength which irradiate a volume approximately 0.5 cm above and below the plane. If the involved breast or initial tumor volume is large, a multiple-plane implant is often required to adequately irradiate the tissue at risk for recurrence. Thus, second, third, or even fourth planes of tubes may be necessary.

Maintaining a uniform interplane distance between the planes of tubes is imperative, if an ideal dose distribution is to be obtained from the afterloaded interstitial radioisotope sources, such as iridium-192 ($^{192}$Ir) seeds. One method of determining the location of the additional planes on the surface of the breast has been by using a ruler. Unfortunately, marking parallel lines on the breast is difficult, due to the variable contours peculiar to each breast surface. Measuring the distance from a previously established plane to a proposed new plane with a ruler is not only very time-consuming, it is often inaccurate. As a result, inhomogeneous isodose distributions within the implanted volume subsequently occur.

Pierquin et al (see "Radical Radiation Therapy of Breast Cancer," *Int. J. Radiat. Oncol. Biol. Phys.*, 1980, vol. 6, pp. 17–24) have described a method obviating the problem of inaccuracy associated with using a ruler by custom-drilling holes for tube insertion locations in a pair of perspex plaques for each patient, with interplane and inter-tube distances being determined pre-operatively. This technique allows proper margins above the patient's ribs and below the skin to be chosen, while maintaining uniform interplane distances. However, the technique has the disadvantage of requiring that a new set of plaques be constructed for each patient, or at best that an extensive selection of different plaque sets be available for use on patients with different breast sizes and tumor volumes.

Martinez et al (see "Irradiation With External Beam and Interstitial Radioactive Implant as Primary Treatment for Early Carcinoma of the Breast," *Surg. Gynecol. Obstet.*, 1981, vol. 152, pp. 285–290), on the other hand, have described the use of a fixed-interval breast bridge which allows marking of the breast at fixed 1 cm intervals in a manner similar to the above-described technique of Pierquin et al. While the fixed-interval bridge can be used for many patients, its inability to provide variable interplane distance selections is a severe drawback, as one is unable to optimize the placement of both the most superficial and the deepest planes relative to the skin and ribs, respectively. Likewise, one is unable to optimize the dose-rate to the implanted sources.

Consequently, a need exists for a more versatile device to locate multiple planes on the breast, the use of which is independent of breast size and shape, and, at the same time, simple, accurate and easy to use.

SUMMARY OF THE INVENTION

The present invention provides an adjustable breast bridge which is designed to satisfy the aforementioned needs. It can be used on breasts of any size and shape to accurately determine and draw the locations of multiple planes on the breast. In other words, by using the bridge one is able to draw a line on the nonuniform, three-dimensional surface of any breast such that the one line drawn on that surface is always the same height in space above the plane beneath it.

The adjustable breast bridge of the present invention incorporates the advantages of the prior techniques of Pierquin et al and Martinez et al, but not their disadvantages. That is, not only can interplane distances be selected according to the individual requirements of each patient, but the same bridge may now be used for all patients. Furthermore, from actual use of the adjustable breast bridge a significant reduction in operating-room time for the implantation procedure has been noted over that required with the fixed-interval bridge. This reduction is due to elimination of the necessity of visually interpolating interplane distances of other than 1 cm. By decreasing operating-room time, both expense to the patient and the risk from prolonged anesthesia have been reduced. Last, and most important, the precision attained by the adjustable breast bridge facilitates the of parallel rows of $^{192}$Ir sources at any selected interplane distance which, in turn, provides for uniform dose distributions at an optimum dose-rate to the volume implanted.

Accordingly, the present invention is directed to an adjustable breast bridge for use on all patients with breast cancer who are to receive multiple-plane interstitial radioisotope implants as a part of their primary treatment. The adjustable breast bridge includes (a) a pair of upright support members; (b) a transverse span member; (c) means for mounting the span member to corresponding upper ends of the upright support members, the mounting means being adjustable for presetting the distance between the support members such that the bridge can straddle a breast of any size; (d) means for receiving a marking tool, the means being mounted to at least one of the support members for movement along the support member toward and away from its lower end; and (e) means for adjustably securing the marking tool receiving means at any desired position along the support member.

More particularly, at least one of the upright support members includes a pair of laterally spaced-apart upright legs and an upper generally transverse arch interconnecting the legs at the upper ends thereof. The legs of the at least one support member define a channel therebetween. The marking tool means is mounted to the one support member within the channel formed by its legs for movement toward and away from its arch. The marking tool receiving means defines an elongated transverse slot through which a marking tool may be extended in a direction toward the opposite support member and into contact with a breast when the bridge is straddling the same. Further, there are distance calibration markings defined on at least one support member, with a reference marking defined on one of the marking tool receiving means, such that the distance of the marking tool from the lower end of the one support member may be determined.

BRIEF DESCRIPTION OF THE DRAWINGS

FIG. 1 is a perspective view of the adjustable breast bridge of the present invention, with a marking tool shown inserted in the bridge as it would be positioned to draw a line along the surface of a breast.

FIG. 4 is an end elevational view of the adjustable breast bridge of FIG. 1.

FIG. 5 is a bottom plan view taken along line 5—5 of FIG. 4, showing a bottom plate on each one of the end support arms of the bridge.

FIG. 6 is a side elevational view of a marking tool support assembly which adjustably mounts in each end support arm of the bridge.

FIG. 7 is a bottom plan view of the marking tool support assembly taken along line 7—7 of FIG. 6.

FIG. 8 is a side elevational view of the marking tool used with the adjustable breast bridge.

FIG. 9 is a top plan view of the tool taken along line 9—9 of FIG. 8.

FIG. 10 is another perspective view of the adjustable breast bridge similar to that of FIG. 1, but showing the bridge in use on a breast.

DETAILED DESCRIPTION OF THE INVENTION

Figure 3:
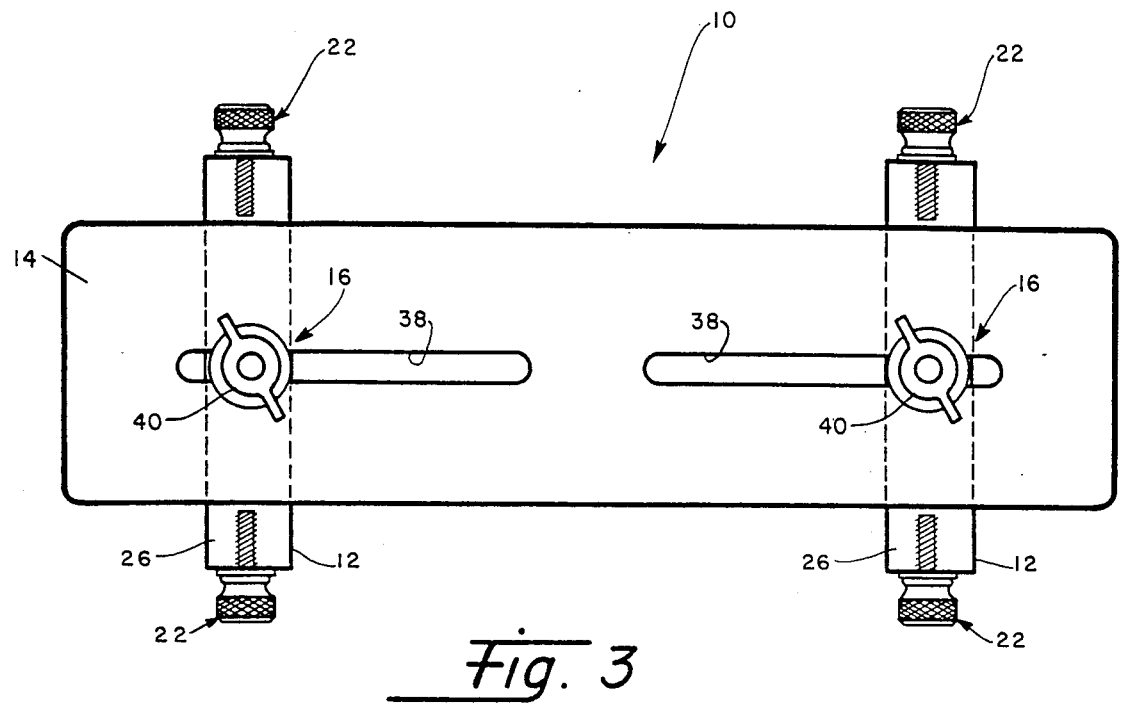
FIG. 3 is a top plan view of the bridge taken along line 3—3 of FIG. 2.
Figure 2:
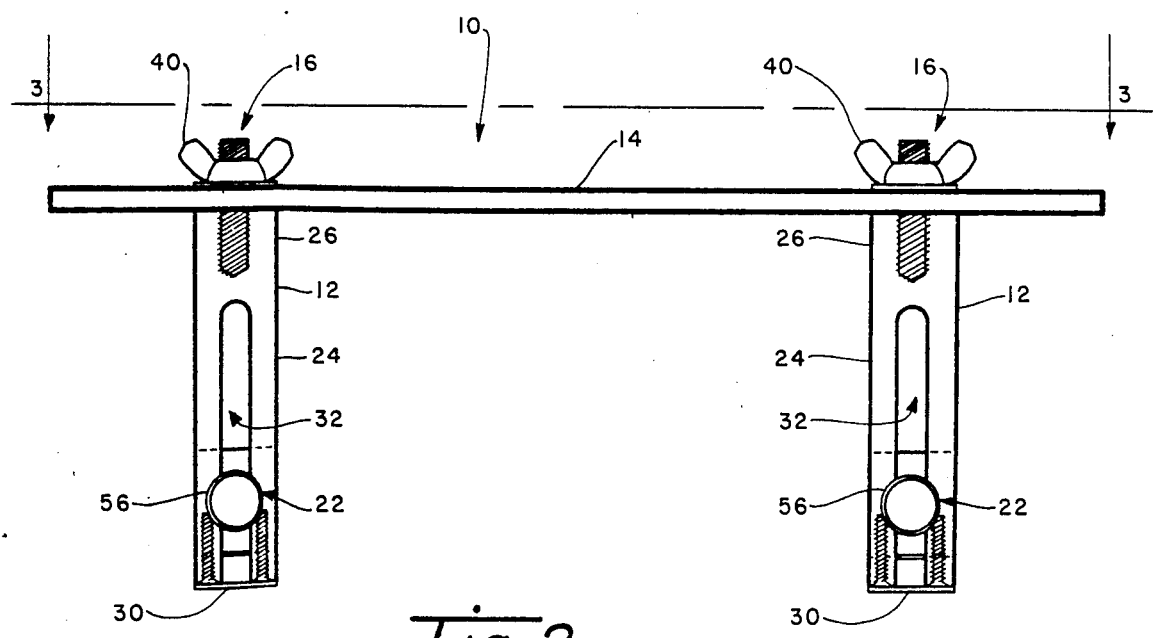
FIG. 2 is a side elevational view of the adjustable breast bridge of FIG. 1.

Referring now to the drawings, and more particularly to FIGS. 1 through 4, there is shown the preferred embodiment of the adjustable breast bridge of the present invention, being generally designated 10. The breast bridge 10 includes a pair of upright end support members 12 and a transverse span member 14, preferably fabricated of Lucite material. Fastening means, generally designated 16, mount the span member 14 to the corresponding upper ends of the support members 12. Guide means, generally designated 18, for receiving a marking tool 20 are mounted on at least one, and preferably both, of the support members 12. Adjustment means, generally designated 22, secure each guide means 20 at any desired position along the corresponding one of the support members 12.

The upright end support members 12 are each generally inverted U-shaped, and comprised of a pair of laterally spaced-apart upright legs 24 and an upper, generally horizontal transverse arch 26 interconnecting the legs 24 at the upper ends thereof. The legs 24 of each support member 12 define a channel 28 therebetween. The lower ends of the legs 24 of each support member 12 are positioned in a common plane with one another and have a flat stainless steel plate 30 (see FIG. 5) attached thereto. Furthermore, the legs 24 of each support member 12 have respective longitudinal guideways 32 defined therein which provides the legs with a bifurcated configuration. That is, the guideways 32 of each support member 12, in addition to being aligned with one another, extend through the legs 24 so as to open at the outer opposite sides 34, as well as at inner facing sides 36, of the legs.

Fastening means 16 which mount the span member 14 to the upper ends of the support members 12 are adjustable for presetting the distance between the support members 12 such that the bridge 10 can straddle a breast of any size. The fastening means 16 takes the form of at least one elongated slot 38, and preferably a pair of slots, defined in the span member 14 as seen in FIG. 1. An adjustable stainless steel wing nut type fastener 40 extends through each slot 38 and is attached to the arch 26 of each support member 12.

Guide means 18 takes the form of a marking tool receiving block 42 made from Lucite material and being mounted in the channel 28 of each support member 12 for generally vertical sliding movement along the legs 24 thereof. Each block 42, as seen also in FIGS. 6 and 7, includes a central portion 44 of reduced cross-sectional width and opposite end portions 46 from which guides 48 outwardly protrude. The guides 48 extend into, and are slidable along, the guideways 32 of the legs 24 of the respective support members 12. The central portion 44 of the block 42 has a rectangular-shaped recess 50 with a flat stainless steel strip 52 bridging the recess and attached at opposite ends to the central portion so as to define an elongated transverse slot 54 in the block 42. The slot 54 is dimensioned to receive the marking tool 20 such that it may be extended in a direction toward the slot 54 of the opposite support member 12 and into contact with a breast B when the bridge 10 is straddle of the same, such as seen in FIG. 10. The slots 54 in the guide means 18 of the pair of support members 12 are in a plane which is parallel to the common plane formed by the flat plates 30 on the lower ends of the legs 24 of the support members 12.

Adjustment means 22 are mounted in the outer ends of the guides 48 of marking tool receiving block 42 and extend beyond the outer sides 34 of the respective legs 24 of the support members 12. The adjustment means 22 preferably take the form of stainless steel friction-lock knobs 56 which are threaded into the guides 48. The knobs 56 may be tightened so as to frictionally engage the outer leg sides 34 for retaining the block 42 at any desired position along the support member 12, and thereby the marking tool 20 at any height above a base, generally designated 58, of the bridge 10 formed by the flat plates 30.

For setting the slots 54, and thereby the marking tool 20, a desired distance from the base 58 of the bridge 10, distance calibration markings 60 are defined on outer end faces 62 of the legs 24 of the support members 12 and a reference mark 64 is defined on the lateral ends of the outer sides of the blocks 42 adjacent the calibration markings 60.

By loosening the friction-lock knobs 56, the position of the slots 54 in blocks 42 may be adjusted to the desired height above the bridge base 58. In such manner, the distance in millimeters of each line to be drawn on opposite sides of a breast from the base of the bridge is determined. The marking tool 20 is slid through the slot 54 and can draw a line on the breast surface through linear movement of the tool 20 along the slot, such as seen in FIG. 10. The width of the slot 54 is only slightly greater than the thickness of the tool 20 so that the tool 20 can only be moved within the common plane formed by the two opposite slots 54. This way the line drawn on the breast surface will be a known precise distance above and parallel to the base 58 of the bridge. After removal of the bridge 10 from the breast, this line will be used as a guide when determining entrance/exit points on the breast for insertion of a new plane of hollow steel trocars.

The method of interstitial implantation of the breast using a removable afterloading technique has been previously described in the Martinez publication. In brief, a tumor volume is established clinically and a computerized preimplant dosimetric plan is used to select the proper spacing between rows of $^{192}$Ir sources and between planes. This spacing is based upon the number and strength of $^{192}$Ir sources to be used, such that a tumor volume dose-rate of 900–1000 rad/day is achieved. Intraoperatively, the deepest or first plane of hollow stainless steel trocars 66 is inserted approximately 1 cm above the chest wall. The location of the next plane is then determined by use of the adjustable breast bridge 10.

Each support member slot 54 is set to the specified interplane distance determined by the preplan. The entire bridge 10 is then placed over or straddle of the breast B (FIG. 10), and arranged so that the base 58 of the bridge 10 rests snugly on the first plane of trocars or needles 66. The felt tip portion 68 of a marking tool 20, such as a sterile commercial operating room pen, is then inserted into a slot 70 at the tip of the marking tool 20, and the tool is placed through one support member slot 54. The tool 20 is then used to lightly draw a line L along the surface of the breast at that level (FIG. 10). A similar line is drawn along the opposite side of the breast, using the other support member slot. Alternatively, a bridge may be used identical to bridge 10 but only having a guide means 18 in one of the support members 12. Once the line is drawn on one side of the breast, the bridge is rotated 180° and then a line can be drawn on the other side of the breast using the same slot 54. The bridge 10 is then removed, and additional trocars 66 are placed through the breast at entrance and exit points marked along these lines, to form the second plane of the implant.

If additional planes are needed, this process can be repeated, each time using the previous plane as a base for the breast bridge, until the desired volume is implanted. After all trocars are in position, they are replaced with hollow nylon tubes, which are subsequently afterloaded with $^{192}$Ir sources. Using this adjustable breast bridge, up to 4 planes have been accurately delineated for subsequent implantation.

In summary, the adjustable breast bridge 10 offers a simple, rapid, inexpensive, and accurate method for localization of planes on the breast surface. The precision of this instrument facilitates the placement of parallel rows of trocars and $^{192}$Ir sources at any selected interplane distance, which in turn provides for uniform dose distributions at an optimum dose-rate to the volume implanted. The bridge can be used effectively in all patients with breast cancer who are to receive a multiple-plane interstitial implant as a part of their primary treatment.

It is thought that the present invention and many of its attendant advantages will be understood from the foregoing description and it will be apparent that various changes may be made in the form, construction and arrangement of the parts thereof without departing from the spirit and scope of the invention or sacrificing all of its material advantages, the form hereinbefore described being merely a preferred or exemplary embodiment thereof.

Having thus described the invention, what is claimed is:

1. In a breast bridge for use in multiple-plane interstitial radioisotope breast implants, said bridge including a pair of upright support members, a transverse span member and means for mounting said span member to corresponding upper ends of said upright support members, the improvement comprising:
   (a) at least one of said upright support members including a pair of laterally spaced-apart upright legs defining a channel therebetween, said legs of said at least one upright support member being bifurcated so as to define respective longitudinal guideways therein which are aligned with one another and extend through said legs so as to open away from said channel at outer opposite sides as well as into said channel at inner facing sides of said legs;
   (b) means for receiving a marking tool being mounted to said at least one of said support members within said channel thereof for movement along spaced-apart upright legs of said support member toward and away from a lower end of said support member, said marking tool receiving means having outwardly-protruding guides on the opposite lateral ends thereof which extend into, and are slidable along, said guideways of said legs of said at least one support member; and
   (c) means for adjustably securing said marking tool receiving means at any desired position along said support member, said means for adjustably securing said marking tool receiving means being mounted to said guides of said latter means at the outer sides of said legs and engagable with said outer leg sides for retaining said marking tool receiving means at any desired position along said support member.

2. The breast bridge as recited in claim 1, wherein said at least one of said upright support members includes an upper, generally transverse arch interconnecting said legs at upper ends thereof.

3. The breast bridge as recited in claim 1, wherein said marking tool receiving means defines an elongated transverse slot through which a marking tool may be extended in a direction toward the opposite support member and into contact with a breast when said bridge is straddle of the same.

4. The adjustable breast bridge as recited in claim 3, wherein said at least one of said upright support members includes a flat plate attached to lower ends of said spaced-apart upright legs so as to provide a base for said support member which is generally parallel to said elongated slot of said marking tool receiving means.

5. The breast bridge as recited in claim 1, wherein said means for adjustably securing said marking tool receiving means comprises a pair of friction-lock knobs which are threaded into said guides to frictionally engage said outer leg sides.

6. The breast bridge as recited in claim 1, wherein said means for mounting said span member to said upper ends of said upright support members includes at least one elongated slot defined in said span member and an adjustable fastener extending through said slot and attached to one of said support members, said slot and fastener rendering said mounting means adjustable for presetting the distance between said support members such that said bridge can straddle a breast of any size.

7. The breast bridge as recited in claim 1, further comprising distance calibration markings defined on one of said marking tool receiving means and said at least one support member, with a reference marking defined on the other, such that the distance of said marking tool from the lower end of said at least one support member may be determined.

8. An adjustable breast bridge for use in multiple-plane interstitial radioisotope breast implants, comprising:
(a) a pair of upright end support members, each of said members having a pair of laterally spaced-apart upright legs and an upper, generally horizontal transverse arch interconnecting said legs at the upper ends thereof, said legs of each support member define a channel therebetween, with the lower ends of both support members being positioned in a first common plane;
(b) a generally horizontal upper span member;
(c) fasteners for adjustably mounting said span member to said arches of said upright support members such that said support members can be preset at a desired distance apart for straddling a breast of a given size;
(d) a marking tool receiving block being mounted in said channel of each of said support members for generally vertical sliding movement along the legs thereof, each block defining an elongated transverse generally horizontal slot through which a marking tool may be extended into contact with a breast for drawing a line thereon, said slots of both blocks being positioned in a second common plane disposed parallel to said first plane of said lower ends of said support members;
(e) means for adjustably securing said marking tool receiving block to its corresponding support member at any desired position along said support member; and
(f) calibration markings defined on said support member legs of said respective support members and reference marks defined on said marking tool receiving block adjacent said calibration markings on said support members for determining the distance of the line to be drawn by said marking tool from said lower ends of said support members.

9. In a multiple-plane interstitial radioisotope breast implantation procedure, a method for accurately determining and drawing the locations of multiple parallel planes on a breast of a patient, comprising the steps of:
(a) inserting a first series of hollow trocars through the breast of the patient, each trocar being inserted at substantially the same predetermined distance above the chest wall of the patient to form a first plane through the breast with said first series of trocars;
(b) positioning lower ends of a pair of laterally-spaced support members of an adjustable breast bridge on said first series of trocars such that said lower support member ends which form a common plane are disposed in said first plane of said first series of trocars and said bridge straddles the breast with its support members disposed on opposite sides of the breast;
(c) inserting a marking tool through an elongated generally horizontal slot defined in each support member, the height of said slots above respective lower support member ends being adjustably preset at the same predetermined distance;
(d) drawing a line with said marking tool on opposite sides of the patient's breast, the lines being located in a plane generally parallel to said first plane;
(e) inserting a second series of hollow trocars through the breast of the patient at the locations of said lines, said second series of trocars forming a second plane through the breast; and
(f) repeating steps (b) through (e) with respect to said second series of trocars to form a third plane through the breast, if desired, and again with respect to a third series of trocars to form a fourth plane through the breast, if desired.

* * * * *